United States Patent [19]
Edell

[11] Patent Number: 4,955,380
[45] Date of Patent: Sep. 11, 1990

[54] FLEXIBLE MEASUREMENT PROBES

[75] Inventor: David J. Edell, Lexington, Mass.

[73] Assignee: Massachusetts Institute of Technology, Cambridge, Mass.

[21] Appl. No.: 285,010

[22] Filed: Dec. 15, 1988

[51] Int. Cl.$^5$ .............................................. A61B 5/00
[52] U.S. Cl. ................... 128/635; 128/736; 204/403; 204/408; 374/178
[58] Field of Search ............... 128/635, 736; 374/178; 204/403, 408

[56] References Cited

U.S. PATENT DOCUMENTS

| | | | |
|---|---|---|---|
| 4,534,356 | 8/1985 | Papadakis | 128/635 |
| 4,587,719 | 5/1986 | Barth | 29/577 |
| 4,741,343 | 5/1988 | Bowman et al. | 128/635 |

FOREIGN PATENT DOCUMENTS

| | | | |
|---|---|---|---|
| 0139589 | 10/1979 | Japan | 374/178 |
| 0109313 | 8/1980 | Japan | 374/178 |

OTHER PUBLICATIONS

Barth et al., "Monolithic Silicon Fabrication Technology for Flexible Circuit and Sensor Arrays," International Electron Devices Meeting Technical Digest, *IEDM 84*:217-219 (1984).

*Primary Examiner*—Lee S. Cohen
*Attorney, Agent, or Firm*—Fish and Richardson

[57] ABSTRACT

Flexible measurement probes are described for the determination of oxygen partial pressure; temperature and perfusion; and combined measurement of oxygen partial pressure, temperature, and perfusion. The probes are fabricated by patterning a metal coated substrate to form a conductive pattern of ribbon leads, insulating the conductive ribbon leads except for contact openings, and then attaching sensors to the conductive ribbon leads through noble metal plated open contacts. The plated contacts may be used directly to measure oxygen partial pressure.

7 Claims, 3 Drawing Sheets

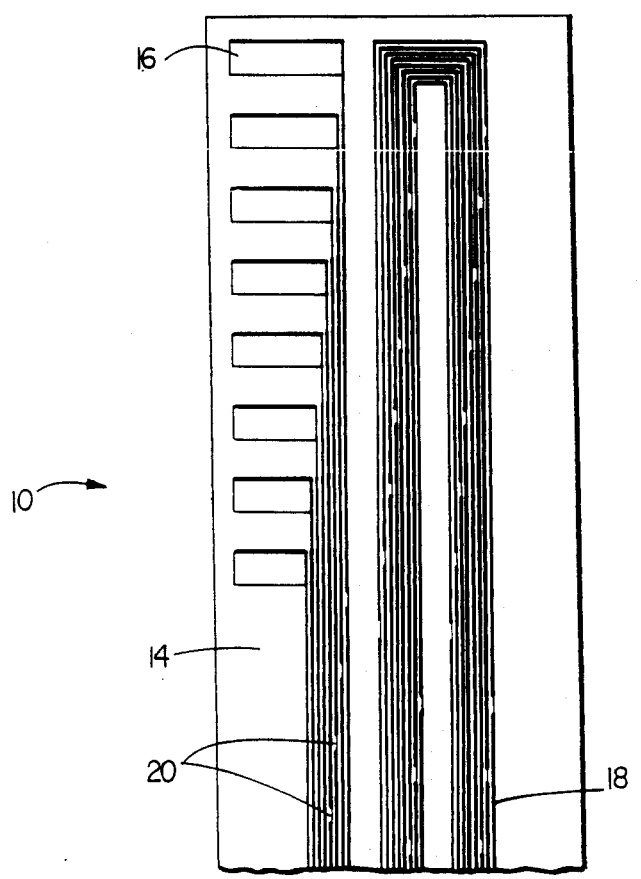
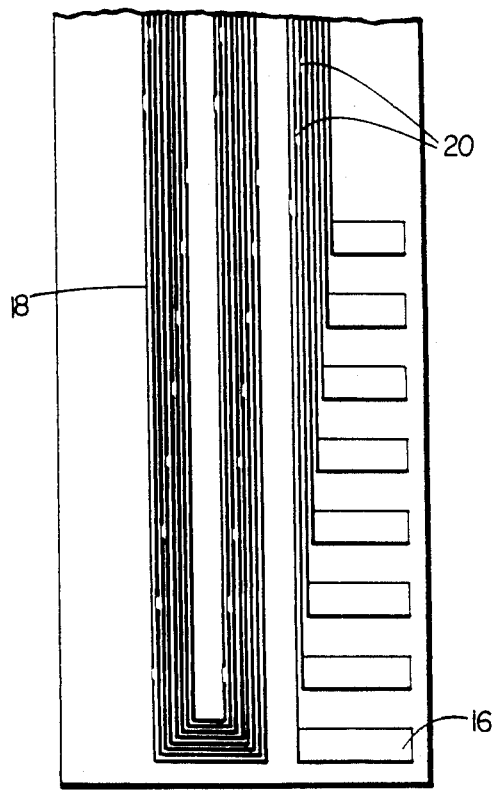
FIG.1

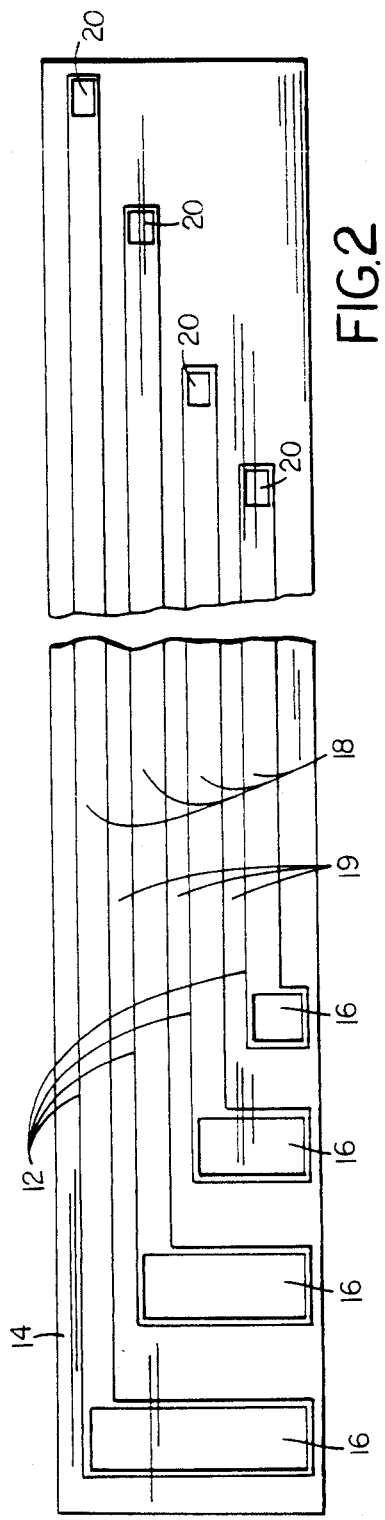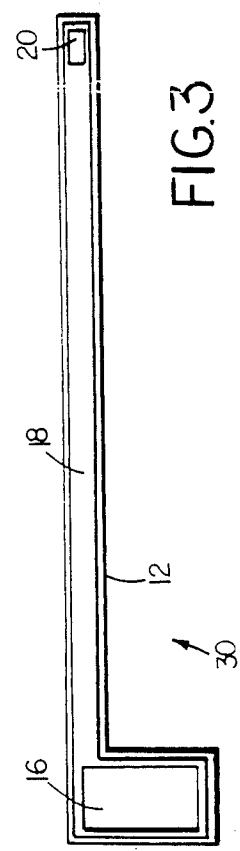

4,955,380

FLEXIBLE MEASUREMENT PROBES

The Government has righs in this invention pursuant to Grant Number NIH-1-RO1-CA37235 awarded by the Department of Health and Human Services.

BACKGROUND

This invention is in the field of measurement probes.

Accurate, multi point measurement of oxygen partial pressure, temperature, and perfusion in tumors and tissues is important clinically. Patients with malignancies not susceptible to surgery, radiation or chemotherapy are often responsive to elevated tumor temperatures resulting from the local application of heat. In precisely selected volumes of tissue that make up the malignancy, specific, well-characterized temperature elevations must be produced, maintained and monitored to be effective. Numerous devices exist to provide for the measurement of temperature, oxygen partial pressure ($pO_2$) and blood perfusion in living tissue. For example, a rigid probe designed to measure $pO_2$ and temperature in body tissue utilizes discrete thermistors, individually placed on the probe substrate. An integrated thin film array on a rigid substrate incorporates temperature sensitive resistors and oxygen sensors. A linear array of diodes on silicon islands supported by a flexible polyimide substrate is used for temperature profile measurement.

SUMMARY OF THE INVENTION

The invention features in one aspect an apparatus for measuring the partial pressure of oxygen which includes a flexible substrate, an electrical conductor which is photolithographically patterned on the substrate, insulation covering the conductor except for a small, exposed contact area, and metal plating on the exposed contact area, in which electrical current flowing through the electrical conductor is correlated with oxygen partial pressure at the metal plating.

In a second aspect the invention features an apparatus for measuring temperature and perfusion which includes two lead assemblies, each lead assembly including a flexible substrate, an electrical conductor photolithographically patterned on the substrate, insulation covering the conductor except for a small, exposed contact area, and a thermal sensor bonded between the small contact areas on the two lead assemblies, in which a voltage drop across the thermal sensor is correlated with temperature and, in which the rate of heat dissipation from the thermal sensor is correlated with perfusion.

In a third aspect the invention features an apparatus for measuring temperature, perfusion, and the partial pressure of oxygen which includes two lead assemblies, each lead assembly including a flexible substrate, an electrical conductor photolithographically patterned on the substrate, and insulation covering the conductor except for a small, exposed contact area; a thermal sensor bonded between the small, exposed contact areas on the two lead assemblies; an additional exposed contact area provided, on one of the lead assemblies, on the side of the flexible substrate opposite the thermal sensor; and metal plating on the additional exposed contact area, in which electrical current flowing through the electrical conductor attached to the metal plating is correlated with oxygen partial pressure at the metal plating, in which a voltage drop across the thermal sensor is correlated with temperature, and in which the rate of heat dissipation from the thermal sensor is correlated with perfusion.

In preferred embodiments of the invention the flexible substrate is polyimide, the electrical conductor is copper, the thermal sensor is a thermistor, and the metal plating is gold. The apparatus includes a plurality of small, exposed contact areas and electrical conductors. The two lead assemblies included in the apparatus for measuring temperature and perfusion or for measuring temperature, perfusion and oxygen partial pressure can be attached.

Flexible measurement probes are inexpensive, disposable, and simple to manufacture. Electrical conductors deposited photolithographically are not susceptible to the stresses imposed by use in living tissue. The measurement probe can be used for oxygen sensing directly after manufacture with no requirement of additional assembly. Using the probe for temperature sensing requires the attachment of one part, a thermistor. This step is easily accomplished as the provision of contact areas surrounded by insulation permits assembly without precise alignment of the thermistor with the contact.

Other features and advantages will be apparent from the following description of the preferred embodiment thereof, and from the claims.

DESCRIPTION OF THE PREFERRED EMBODIMENTS

We first briefly describe the drawings.

Drawings

FIG. 1 is a view of measurement probe ribbon leads patterned on polymer sheets;

FIG. 2 is a detail plan view, not to scale, of the connector and contact ends of ribbon leads;

FIG. 3 is a plan view, not to scale, of an oxygen sensor;

Figure 4:
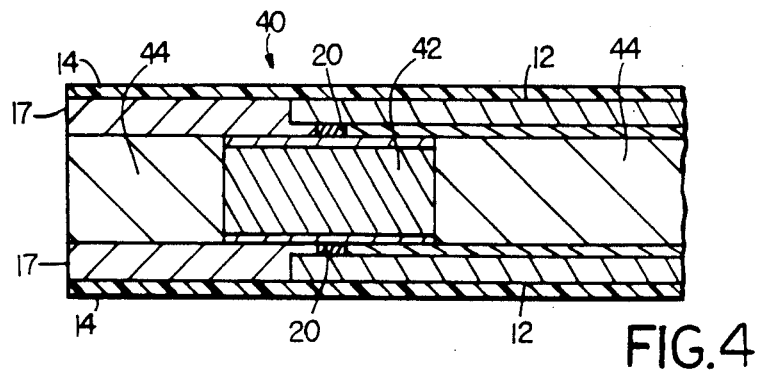
FIG. 4 is a side sectional view, not to scale, of a thermistor assembly for a temperature and perfusion sensor.

The flexible measurement probes can be divided into three groups: oxygen sensors, temperature and perfusion sensors, and oxygen, perfusion and temperature sensors. The probes are fabricated by patterning a metal coated substrate to form a conductive pattern of ribbon leads, insulating the conductive ribbon leads except for contact openings, and then attaching sensors to the conductive ribbon leads through noble metal plated open contacts. Final insulation of the sensors may be required to complete assembly.

Referring to FIGS. 1 and 2, individual measurement probe ribbon leads 12 are laid down in a serpentine pattern 10, 3 mm wide×30 mm long, on a 25 $\mu$m thick flexible polymeric substrate 14 such as Kapton TM (a Dupont material made primarily of polyimide) by first bonding a 25 $\mu$m coating of copper or other suitable conductive material to one side of the substrate with an epoxy or other suitable adhesive. Next, the copper film is patterned using a standard photolithographic technique such as coating the film with photoresist, selectively exposing the photoresist using ultraviolet light illumination through a pre patterned glass mask, developing the transferred image, and then chemically etching the exposed copper. The copper pattern is then cleaned of photoresist, and re-coated with another photosensitive polymer. This second coating is then patterned as above and left in place to form an insulation barrier 17 (see FIGS. 4 and 5) and to define open contact areas 20. The resulting ribbon leads 12 have 1 mm wide edge connectors 16 attached to 75 μm wide (with 100 μm spacing 19) conductor ribbons 18 which are insulated except for small 50 μm×100 μm contact areas 20 for plating for oxygen sensing or for the attachment of temperature sensors or other connectors. Depending on the exact nature of assembly and intended use, the patterns may be cut into specific configurations (FIG. 2) and the openings may be plated with gold, nickel, platinum, or other suitable material.

Referring also to FIG. 3, an oxygen sensor 30 is made from one ribbon lead 12 cut from pattern 10. The sensor contains a connector 16, conductor ribbon 18, and contact area 20, over which is plated a noble metal, for example, gold or platinum.

Referring also to FIG. 4, a temperature/perfusion sensor 40 is assembled by attaching a thermal measurement device 42, such as a thermistor, a diode, or an integrated circuit temperature sensor, between contact areas 20 of two ribbon leads 12 cut from pattern 10, by using a variety of techniques such as soldering, gluing with conductive epoxy or some other suitable conductive adhesive, or thermosonically bonding with gold or other die attach material. The sensor is insulated with epoxy or some other insulating adhesive filling in the space 44 between the ribbon leads. Alternatively, the ribbon leads could be left attached when cut from the pattern and then wrapped around the thermistor.

Figure 5:
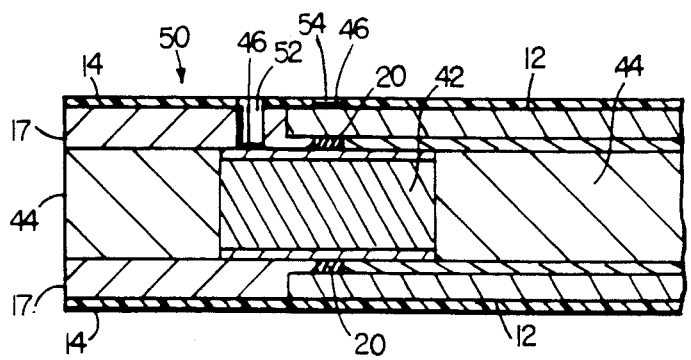
FIG. 5 is a side sectional view, not to scale, of a thermistor assembly and oxygen sensor for a combined oxygen, temperature, and perfusion sensor.

Referring also to FIG. 5, a composite temperature/perfusion and oxygen sensor 50 is fashioned by modifying a temperature/perfusion sensor 40 made as described above, so as to open a backside contact 52 or 54 through the polymer substrate to one conductor or to the thermal measurement device metal contact surface; and then plating gold 46 or other suitable material onto this contact area. Alternately, a ribbon lead 12 is prepared with double sided patterning to produce an oxygen contact opening on the back side of the polymer lead pattern before the temperature sensor is assembled, or a third ribbon lead is attached back to back with one of the other two, to the same effect.

Use

Embedded in living tissue, for example, a tumor, the measurement probes can be used to monitor hyperthermia treatment for malignancies which have failed to respond to surgery, radiation, and/or chemotherapy.

In an oxygen sensor, either the independent or combined probe, oxygen reacts with the metal plating over the electrical conductor to generate an electrical current which is proportional to oxygen partial pressure.

In a temperature sensor, the thermal sensor has a temperature sensitive resistor which exhibits resistance as a function of temperature. The voltage drop across the resistor is then correlated with temperature.

Perfusion measurements are determined by correlating the rate of heat dissipation from the thermal sensor with blood flow.

The measurement probes can also be used for profiling temperature, perfusion, and oxygen partial presure in other applications such as food processing and air exchange system.

Other embodiments are within the following claims. For example, other suitable substrate materials may be teflon or mylar, and other conductive materials may be nickel or platinum.

I claim:

1. Apparatus for measuring temperature and perfusion comprising
    two lead assemblies, each lead assembly comprising
        a flexible substrate,
        an electrical conductor photolithographically patterned on said substrate, and
        insulation covering said conductor except for a small, exposed contact area, and
    a thermal sensor bonded between said small contact areas on said two lead assemblies,
    wherein a voltage drop across said thermal sensor is correlated with temperature, and
    wherein a voltage drop of heat dissipation from said thermal sensor is correlated with perfusion.

2. Apparatus for measuring temperature, perfusion, and the partial pressure of oxygen comprising
    two lead assemblies, each lead assembly comprising
        a flexible substrate,
        an electrical conductor photolithographically patterned on said substrate, and
        insulation covering said conductor except for a small, exposed contact area;
    a thermal sensor bonded between said small, exposed contact areas on said two lead assemblies,
    an additional exposed contact area provided, on one of said lead assemblies, on the side of said flexible substrate opposite said thermal sensor; and
    metal plating on said additional exposed contact area,
    wherein electrical current flowing through said electrical conductor attached to said metal plating is correlated with oxygen partial pressure at said metal plating,
    wherein a voltage drop across said thermal sensor is correlated with temperature, and
    wherein the rate of heat dissipation from said thermal sensor is correlated with perfusion.

3. The apparatus of claim 2 or 3 wherein said two lead assemblies are attached.

4. The apparatus of claim 1 or 2 wherein said flexible substrate is polyimide.

5. The apparatus of claim 1 or 2 wherein said electrical conductor is copper.

6. The apparatus of claim 1 or 2 wherein said thermal sensor is a thermistor.

7. The apparatus of claim 2 wherein said metal plating on said exposed contact area comprises gold.

* * * * *

UNITED STATES PATENT AND TRADEMARK OFFICE
CERTIFICATE OF CORRECTION

PATENT NO. : 4,955,380
DATED : September 11, 1990
INVENTOR(S) : David J. Edell

It is certified that error appears in the above-identified patent and that said Letters Patent is hereby corrected as shown below:

Column 1, line 1, "righs" should be --rights--.
Column 4, Claim 1, line 27, "a voltage drop" should be --the rate--.
Column 4, Claim 3, line 51, "2 or 3" should be --1 or 2--.

Signed and Sealed this

Nineteenth Day of May, 1992

Attest:

DOUGLAS B. COMER

*Attesting Officer*　　　*Acting Commissioner of Patents and Trademarks*